US006231569B1

(12) United States Patent
Bek et al.

(10) Patent No.: US 6,231,569 B1
(45) Date of Patent: May 15, 2001

(54) DUAL PROCESSOR ARCHITECTURE FOR ELECTRO GENERATOR

(75) Inventors: Robin Bek, Campbell; David Wills; Franklin R. Koenig, both of Palo Alto, all of CA (US)

(73) Assignee: Somnus Medical Technologies, Inc., Sunnyvale, CA (US)

( * ) Notice: Subject to any disclaimer, the term of this patent is extended or adjusted under 35 U.S.C. 154(b) by 0 days.

(21) Appl. No.: 09/167,508

(22) Filed: Oct. 6, 1998

Related U.S. Application Data

(60) Provisional application No. 60/061,714, filed on Oct. 6, 1997, provisional application No. 60/062,458, filed on Oct. 6, 1997, provisional application No. 60/061,193, filed on Oct. 6, 1997, provisional application No. 60/061,197, filed on Oct. 6, 1997, provisional application No. 60/062,543, filed on Oct. 6, 1997, and provisional application No. 60/061,213, filed on Oct. 6, 1997.

(51) Int. Cl.[7] .................................................. A61B 18/18
(52) U.S. Cl. ........................ 606/34; 606/41; 607/102; 128/923
(58) Field of Search ................................ 607/96, 98–102; 606/34, 35, 38, 41, 42, 31, 48, 50; 128/902, 905, 920, 922, 923; 600/513, 123

(56) References Cited

U.S. PATENT DOCUMENTS

| 5,233,515 | 8/1993 | Cosman | 364/413.02 |
| 5,868,737 | * 2/1999 | Taylor et al. | 606/34 |
| 5,871,481 | * 2/1999 | Kannenberg et al. | 606/34 |

FOREIGN PATENT DOCUMENTS

| WO 97/20510 | 6/1997 | (WO) | A61B/17/39 |

* cited by examiner

*Primary Examiner*—Lee Cohen
*Assistant Examiner*—David M. Ruddy
(74) *Attorney, Agent, or Firm*—Wilson Sonsini Goodrich & Rosati

(57) ABSTRACT

The present invention provides for an electro-surgical instrument with a rich graphical user interface (GUI) capability and a verifiable hardware and software platform meeting Food and Drug Administration (FDA) requirements. The rich GUI makes for a device which is more easily operated than prior art devices which lacked a sophisticated user interface. The increased functionality is achieved without sacrificing the ability to validate the device for FDA purposes. This goal is achieved by a dual processor design. In the dual processor design a control or master processor with verifiable source code implements the functions of: power delivery, temperature measurement, power measurement and power control. A display or slave processor, is functionally isolated from the first processor receiving only messages from the first processor.

In a first embodiment of the invention an electro-surgical instrument is disclosed. The electro-surgical instrument includes a power delivery channel, at least one electrode and a display. The electro-surgical instrument also includes a control unit and a display unit. The control unit controls the operation of the power delivery channel and at least one electrode to deliver power to the surgical site. The control unit also determines at least one parameter of the power delivery channel and passing the parameter to the display unit. The display unit is coupled to the control unit and the display. The display unit accepts the at least one parameter, generates the graphical user interface on the display and displays the at least one parameter on the graphical user interface.

In another embodiment of the invention a method for providing a graphical user interface in an electro-surgical instrument is disclosed.

5 Claims, 11 Drawing Sheets

| Byte # | Content |
|---|---|
| - | FS (optional) |
| 0 | 'P' |
| 1 | state |
| 2 | parameter |
| 3 | value, low byte |
| 4 | value, high byte |
| 5 | CRC, low byte |
| 6 | CRC, high byte |
| 7 | FS (mandatory) |

FIG. 6A

| Parameter | Value |
|---|---|
| Target Temperature | 'T' |
| Maximum Power | 'P' |
| Endpoint Energy | 'E' |
| Endpoint Time | 'S' |
| Model Select | 'M' |

FIG. 6B

| Byte # | Content |
|---|---|
| - | FS (optional) |
| 0 | 'D' |
| 1 | state |
| 2 | burn time, LSB |
| 3 | burn time, MSB |
| 4 | RF Channel #0 power, LSB |
| 5 | RF Channel #0 power, MSB |
| 6 | RF Channel #0 total energy, LSB |
| 7 | RF Channel #0 total energy, MSB |
| 17 | temperature channel #0, MSB |
| 18 | temperature channel #1, LSB |
| 19 | temperature channel #1, MSB |
| 20 | temperature channel #2, LSB |
| 21 | temperature channel #2, MSB |
| 22 | temperature channel #3, LSB |
| 23 | temperature channel #3, MSB |
| 24 | temperature channel #4, LSB |
| 25 | temperature channel #4, MSB |
| 44 | temperature channel #14, LSB |
| 45 | temperature channel #14, MSB |
| 46 | temperature channel #15, LSB |
| 47 | temperature channel #15, MSB |
| 48 | temperature channel #16, LSB |
| 49 | temperature channel #16, MSB |
| 50 | temperature channel #17, LSB |
| 51 | temperature channel #17, MSB |
| 52 | CRC, low byte |

FIG. 7

DUAL PROCESSOR ARCHITECTURE FOR ELECTRO GENERATOR

CROSS REFERENCE TO RELATED APPLICATION

This application claims the benefit of prior filed copending Provisional Application No. 60/061,714, filed on Oct. 6, 1997, entitled Dual Processor Architecture For Electrosurgical Generator, Provisional Application No. 60/062,458, filed on Oct. 6, 1997, entitled Linear Power Control With Digital Phase Lock, Provisional Application, Provisional No. 60/061,193, filed on Oct. 6, 1997, entitled Linear Power Control With PSK Regulation, Provisional Application No. 60/061,197, filed on Oct. 6, 1997, entitled Memory for Regulating Device Utilization and Behavior, Provisional Application No. 60/062,543, filed on Oct. 6, 1997, entitled Method And Apparatus For Power Measurement In Radio Frequency Electro-Surgical Generators, and Provisional Application No. 60/061,213, filed on Oct. 6, 1997, entitled Method And Apparatus for Impedance Measurement In A Multi-Channel Electro-Surgical Generator.

The present application is related to copending U.S. patent application Ser. No. 09/167,217, filed Oct. 6, 1998, entitled Linear Power Control With Digital Phase Lock, U.S. patent application Ser. No. 09/167,217, filed Oct. 6, 1998, entitled Linear Power Control With PSK Regulation, U.S. patent application Ser. No. 09/167,222, filed Oct. 6, 1998, entitled Memory for Regulating Device Utilization and Behavior, U.S. patent application Ser. No. 09/167,505, filed Oct. 6, 1998, entitled Method And Apparatus For Power Measurement In Radio Frequency Electro-Surgical Generators, U.S. patent application Ser. No. 09/167,215, filed Oct. 6, 1998, entitled Method And Apparatus for Impedance Measurement In A Multi-Channel Electro-Surgical Generator, International Application No. PCT/US98/21065, filed Oct. 6, 1998, entitled Linear Power Control With Digital Phase Lock, and International Application No. PCT/US98/21061, filed October 1998, entitled Dual Processor Architecture For Electro Generator.

Each of the above-cited applications is incorporated herein by reference in its entirety.

SUMMARY OF THE INVENTION

1. Field of the Invention

This invention relates to the field of electro-surgical medical devices. More particularly, this invention relates to devices that deliver energy in the form of radio-frequency electrical current to tissue in order to perform surgical functions.

2. Description of Related Art

Various medical procedures rely on high-frequency electrical currents to deposit energy and thus heat human and animal tissues. During such procedures, a high-frequency current is passed through the tissue between electrodes. One electrode is located at the tip of a surgical probe. Another electrode is located elsewhere, and may be a ground pad or another surgical probe tip. The tissue to be treated lies between the electrodes.

When the electrode circuit is energized, the electric potential of the electrodes at the probe tips oscillates at radio frequencies about a reference potential. If one is used, a ground pad remains at a floating reference potential. As the electric potential of the probe electrodes varies, a motive force on charged particles in the tissue is established that is proportional to the gradient of the electric potential. This electromotive force causes a net flow of electric charge, a current, to flow from one electrode, through the tissue, to any other electrode(s) at a lower potential. In the course of their flow, the charged particles collide with tissue molecules and atoms. This process acts to convert electrical energy to sensible heat in the tissue and is termed Joule heating.

Upon heating, surgical functions such as cutting, cauterizing and tissue destruction can be accomplished. For example, tissues can be cut by heating and eventually vaporizing the tissue cell fluids. The vaporization causes the cell walls to rupture and the tissue to cleave. When it is beneficial to destroy tissue, comparatively higher rates of energy deposition can cause tissue ablation.

Ablation of cellular tissues in situ is used in the treatment of many diseases and medical conditions either alone or combined with surgical removal procedures. Surgical ablation is often less traumatic than surgical removal procedures and may be the only alternative where other procedures are unsafe.

The Food and Drug Administration (FDA) requires an extensive validation process for approval of radio frequency (RF) electro-surgical devices. This evaluation is designed to assure that any risks associated with this type of surgical procedures are minimized. The validation process requires documenting and testing all possible states and exceptions that can be generated by the combined hardware and software that makes up the RF Electro-Surgical device. Depending on the level of concern every line of source code must be documented to the satisfaction of the FDA. The degree to which computer controlled medical equipment is verified and validated depends on the level of concern. These levels of concern can also be applied to subsystems within a system. This latter requirement has prevented the introduction of complex graphical user interfaces (GUIs) for electro-surgical devices. Complex graphical user interfaces are certainly available on personal computers. These interfaces are generated using the proprietary software of companies such as Microsoft, e.g. Windows 95® and Apple Computer, e.g. System 7®. However, the source code for these well know operating systems is proprietary and thus can not be verified to the satisfaction of the FDA. Absent the use of these complex operating systems and development environments they provide, companies manufacturing electro-surgical devices have been limited in the complexity of their GUIs to those which can be generated with source code written in house. Typically electro-surgical device displays are limited to one or two lines of alphanumeric display without any graphical capability.

What is needed is a way to create for electro-surgical instruments the more user-friendly GUIs found in Microsoft's or Apple's operating environments while staying in compliance with FDA guidelines for computer controlled surgical equipment.

SUMMARY OF THE INVENTION

The present invention provides for an electro-surgical instrument with a rich graphical user interface (GUI) capability and a verifiable hardware and software platform meeting Food and Drug Administration (FDA) requirements. The rich GUI makes for a device which is more easily operated than prior art devices which lacked a sophisticated user interface. The increased functionality is achieved without sacrificing the ability to validate the device for FDA purposes. This goal is achieved by a dual processor design. In the dual processor design a control or master processor with verifiable source code implements the functions of:

power delivery, temperature measurement, power measurement and power control. A display or slave processor, is functionally isolated from the first processor receiving only messages from the first processor.

In a first embodiment of the invention an electro-surgical instrument is disclosed. The electro-surgical instrument includes a power delivery channel, at least one electrode and a display. The electro-surgical instrument also includes a control unit and a display unit. The control unit controls the operation of the power delivery channel and at least one electrode to deliver power to the surgical site. The control unit also determines at least one parameter of the power delivery channel and passing the parameter to the display unit. The display unit is coupled to the control unit and the display. The display unit accepts the at least one parameter, generates the graphical user interface on the display and displays the at least one parameter on the graphical user interface.

In another embodiment of the invention a method for providing a graphical user interface in an electro-surgical instrument is disclosed. The electro-surgical instrument includes a power delivery channel, at least one electrode and a display. The method for providing comprises the acts of:

controlling with a control unit the operation of the power delivery channel and at least one electrode to deliver power to the surgical site;

determining with the control unit at least one parameter of the power delivery channel;

passing the at least one parameter from the control unit to a display unit;

accepting at the display unit the at least one parameter; and displaying the at least one parameter on a graphical user interface generated by the display unit.

BRIEF DESCRIPTION OF THE FIGURES

The above and other objects and advantages of the invention will be apparent upon consideration of the following detailed description, taken in conjunction with the accompanying drawings, in which like reference numerals refer to like parts throughout.

FIGS. 6A–B show the data structures associated with the header of the messages passed from the master processor to the slave processor.

FIG. 7 shows the data structure of a data payload portion of a message.

DETAILED DESCRIPTION

The present invention provides for an electro-surgical instrument with a rich graphical user interface (GUI) capability and a verifiable hardware and software platform meeting Food and Drug Administration (FDA) requirements. The rich GUI makes for a device which is more easily operated than prior art devices which lacked a sophisticated user interface. The increased functionality is achieved without sacrificing the ability to validate the device for FDA purposes. This goal is achieved by a dual processor design. In the dual processor design a control or master processor with verifiable source code implements the functions of: power delivery, temperature measurement, power measurement and power control. A display or slave processor, is functionally isolated from the first processor receiving only messages from the first processor. These messages contain control parameters and data which allow the display processor to update the complex GUI's it displays during the course of a surgical operation. The display processor must respond to the control processor within a defined period of time. The display processor also verifies the data integrity by use of a cyclical redundancy check (CRC) algorithm. The GUI's are created in a complex operating environment which is proprietary and un-verifiable. That operating system can, for example, be Windows 95® by Microsoft, or System 7®, by Apple Computer.

Figure 1:
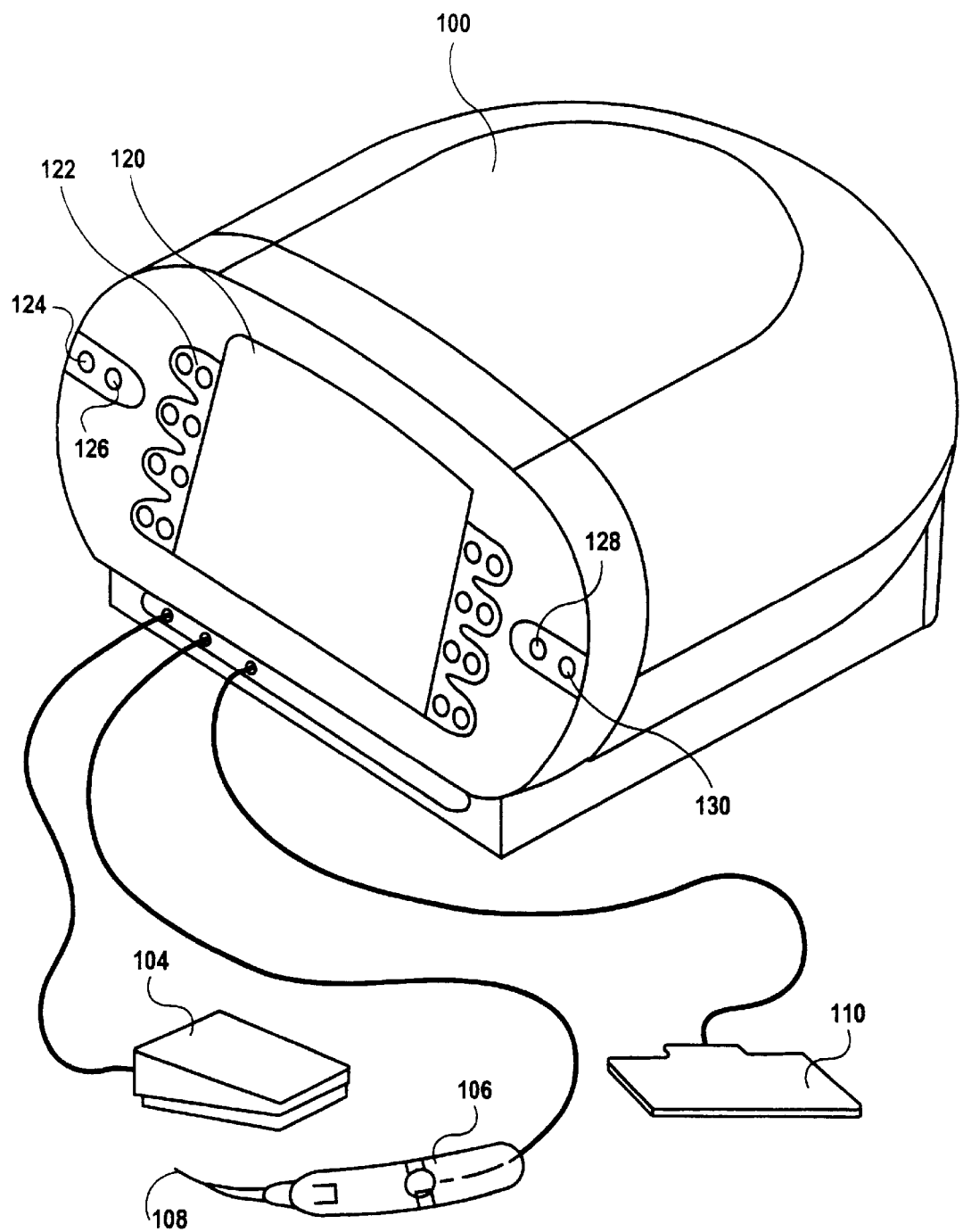
FIG. 1 is an isometric view of an electro-surgical device.

FIG. 1 shows an exterior isometric view of an embodiment of the electro-surgical generator. The electro-surgical generator includes a housing 100, an instrument 106, a ground pad 110 and a foot switch 104. The electro-surgical instrument 106 includes a probe 108, the tip of which may include one or more electrodes. The housing includes a color display 120, a series of front panel parameter control buttons 122, a stand-by/ready button 126, a ready indicator light 124, an RF power delivery indicator light 128 and a fault indicator light 130.

Figure 2:
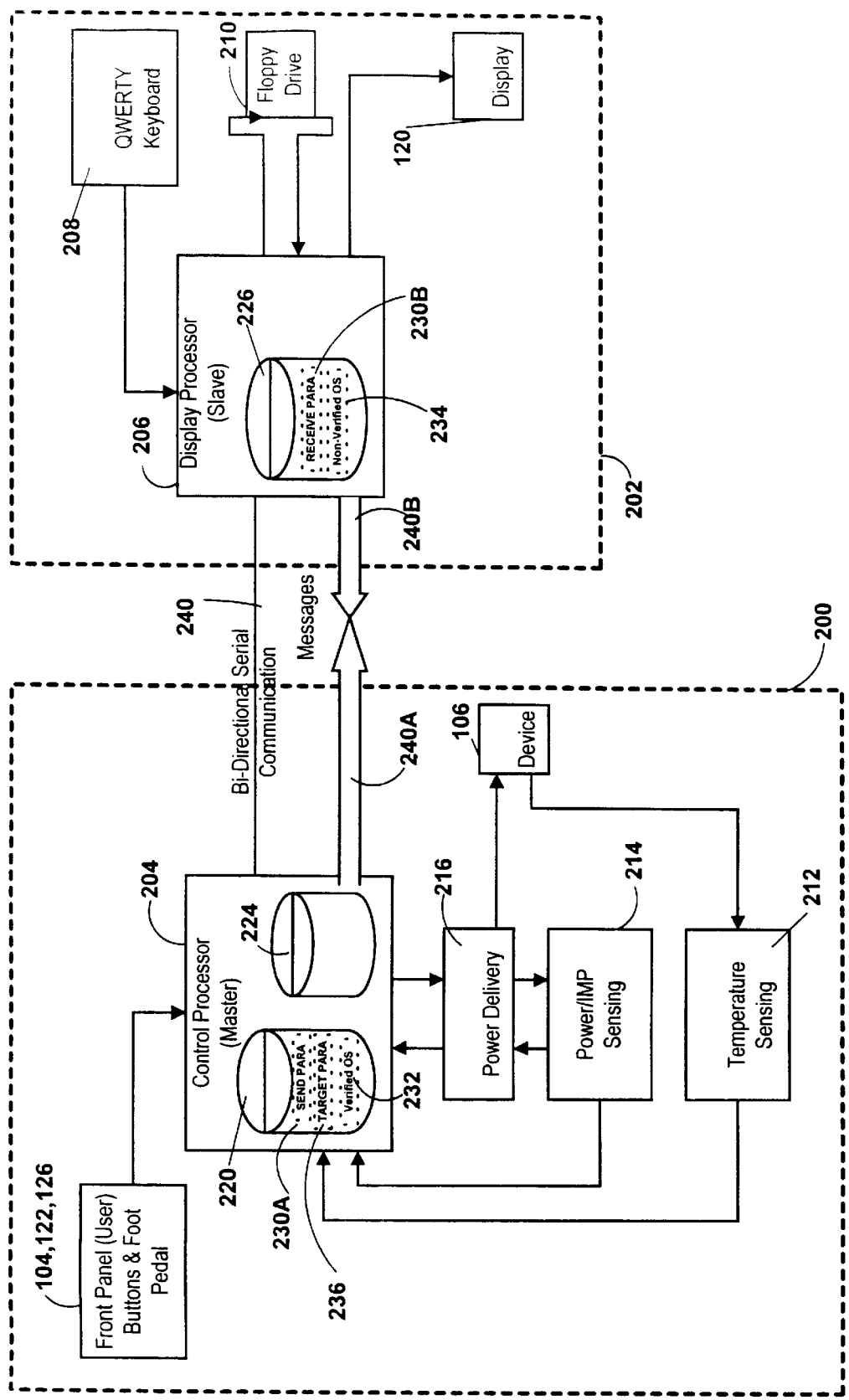
FIG. 2 is a hardware block diagram of the dual processor design of the current invention including a master processor for controlling power delivery and measurement and a slave processor for handling display of GUIs.

The housing contains both the RF delivery and control/master processor as well as the slave/display processor (see FIG. 2). The foot switch 104, the instrument 106 and the ground pad 110 are all coupled to the housing with flexible connectors.

The electro-surgical device is placed in operation by user's activation of a power switch [not shown]. The surgical instrument 106 and specifically the probe portion 108 thereof is placed in contact with the patient at the appropriate surgical site. The probe may be delivered to the site directly through an opening or incision or may be guided to the surgical site through a catheter.

After the appropriate diagnostics, the surgeon is able to move from the standby state in which operating parameters are entered, to the ready state in which parameters are set and power is not delivered to the instrument 106. The foot switch is also used to toggle the device between the ready and the operating state in which power is supplied to the surgical site. Details on the actual GUIs of an embodiment of the invention are displayed on display 120 (see FIGS. 8–9).

FIG. 2 is a hardware block diagram of the dual processor design of the current invention. A power control and measurement unit 200 and a display unit 202 are shown. The power control and measurement unit 200 includes the control/master processor 204, a power delivery module 216, a power and impedance sensing circuit 214, temperature sensing circuit 212, the surgical instrument 106 as well as inputs from both the front panel control buttons 122,126 and the foot switch 104. The control processor 204 interfaces with nonvolatile memory 220 and volatile memory 224. Memory 220 includes the verified operating system 232 comprising in house source code. The memory 220 also includes control/target parameter file 236 and code for sending parameters 230A from the master processor 204 to the slave processor 206. The control parameter database contains operating parameters for a surgical procedure as a function of time. Thus a profile of temperature vs. time, power vs. time, and impedance vs. time is contained in this database, in this embodiment of the invention.

The display unit 202 includes the display/slave processor 206, a keyboard 208, a floppy drive 210 and the display 120 (see FIG. 1). The slave processor interfaces with memory 226. Memory 226 contains code for receiving parameters 230B at the slave processor from the master processor. Memory 226 also contains a proprietary operating system such as Windows 95® which is capable of supporting a complex GUI environment.

The front panel buttons 122, 126 are direct connected to the control processor 204 as is the foot switch 104. These inputs allow the user to vary desired operating states of the system (see FIG. 3). The power delivery module 216 is coupled to the control processor 204, the surgical instrument 106 and to the power and impedance sensing circuit 214. The power and impedance measurement circuit is also coupled directly to the control processor. The temperature sensing circuit 212 is coupled to both the surgical instrument 106 and the control processor 204.

A bidirectional bus to serial bus connects 240 connects the control processor 204 to the display unit 202 The display processor 202 is coupled to the keyboard 208, the floppy drive 210 and the display 120 (see FIG. 1). The keyboard can be used to enter patient name and record so that that information along surgical history can be stored on a floppy disc.

In operation the control processor 204 initiates the power-up and self-testing when a power-switch is enabled (not shown). After diagnostics have run the system is in standby mode and as such can accept adjustments by the surgeon to operating parameters such as time of operation and total energy. When the user transitions operation to ready mode by pressing the ready/standby button 126 the system enters ready mode. In ready mode the parameters are set. The system can then be moved to the operational mode using the foot switch 104. The control processor working with the control parameters stored in the control/target parameter file 236 or with user inputs from the front panel parameter control buttons 122 determines the appropriate control parameters for the operation from the control parameter code and the elapsed time since start of surgery. As the surgery progresses the power control and measurement unit 200 maintains the drive level of each RF channel at the level indicated in the control/target parameter file 236.

For successive intervals throughout the operation new control parameters, e.g. target temperature or target power are downloaded to the power delivery module 216. The power delivery module 216 accepts from the power/impedance sensing circuit 214 an indication of the actual power delivered and compares that with the target power to calculate current and cumulative error. Then in an embodiment of the invention the power delivery module, using control algorithms such as proportional integral derivative (PID) adjusts the power delivery to the surgical instrument 106 in a manner to minimize the difference between the actual power delivered to the surgical instrument and the target power to be delivered.

An additional degree of safety is provided by sensors positioned in the surgical instrument 106 which allow temperature sensing circuit 212 to monitor the temperature of the tissue at the surgical site. If the temperatures exceed acceptable levels the control/master processor 204 may implement processes to abort power delivery. All of the above-mentioned processes take place independently of the display unit 202.

The only communications passed between the power control and measurement unit 200 and the display unit 202 are messages 240A–B which will be described in greater detail in the following FIGS. 4–7. These messages are passed by program code for sending parameters 230A and by program code 230B for receiving messages contained in respectively the memory of the control processor 204 and the display processor 206. Parameters such as total RF delivery time, impedance, power, energy, tip temperature, etc. are passed from the master control processor 204 to the display processor 206 for display to the user on display 120 (see FIG. 1). The optional keyboard 208 allows the user to input new GUI interfaces and non-verifiable code into display memory 226. The floppy drive allows changes and/or additions to the non-verifiable program code 234 to be uploaded to the display processor. Neither the keyboard nor floppy drive provides an input path to the control processor 204 or more generally the power control and measurement unit 200.

Figure 3:
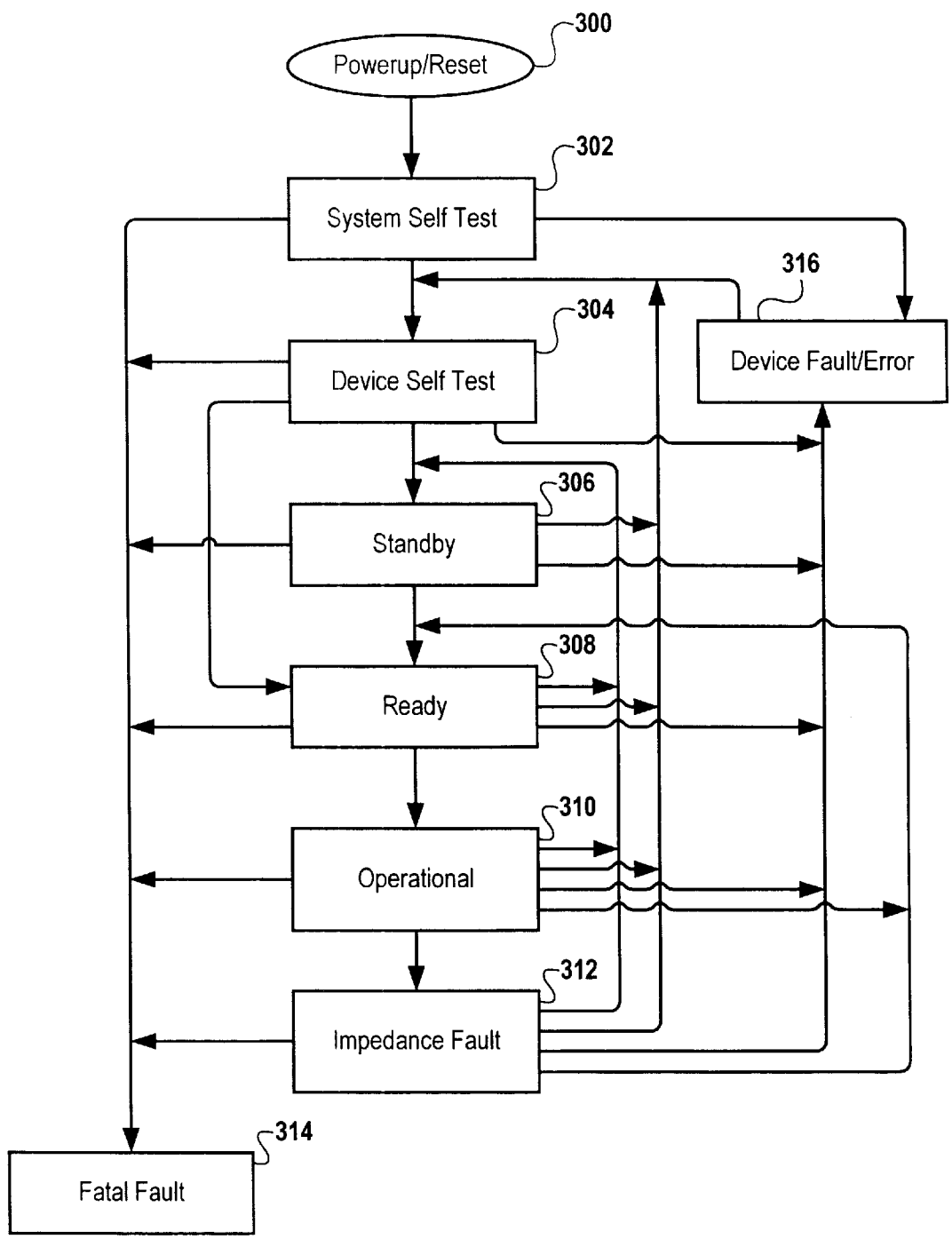
FIG. 3 is a state diagram for the electro-surgical device.

FIG. 3 is a process flow diagram of the major states for the verified operating system (OS) 232 in the power control and delivery module. Processing begins at process 300 in which a power-up reset operation is performed. After a power-up reset the control processor awaits the first acknowledge from the display processor indicating that the display processor is awake and ready to communicate. Control then passes to process 302 and 304 in which respectively a system self-test and a device self-test are performed. Various functions are performed such as testing of the various memories in the control processor, testing of the keyboard for stuck keys, measurement of various system temperatures, power supply voltages, and so forth, to ascertain the general health of the system. If a fatal fault is detected in either of these processes, control passes to process 314 in which the operation of the system is aborted. If a non-fatal fault in the device is detected control is passed to state/process 316. A non-fatal fault in the device might, for example, include a foot switch which was depressed or a surgical instrument 106 which had not yet been connected to the housing 100 (see FIG. 1).

Control then passes to state/process 306 when the system diagnostics have been successfully completed. In the standby phase global parameters are set to default or lowest values and additional user input to change these parameters is accepted from the front panel parameter control buttons 122 (see FIG. 1). The user is thus able to increase or decrease parameters such as: total bum time, maximum impedance, maximum power, maximum energy, maximum temperature, total energy delivered, and total time of delivery. The user may also select the control/target parameter file 236 to be utilized by the surgical instrument to control the surgical procedure.

The surgical device remains in the stand-by or idle state until the user enables ready/standby button 126 or the foot switch 104 to transition from the stand-by to the ready state 308 on the front of housing 100 (see FIG. 1). The system is transitioned from the ready state 308 to the operational state 310 by the user's subsequent toggling of the foot switch 104 (see FIG. 1). Toggling of the foot switch moves the system back to the ready state 308 from the operational state. This assures that the system can be deactivated at any time without resetting the values of the control parameters to a default state. This allows the subsequent reactivation of the system.

The user can change parameters such as maximum temperature, power, total procedure time and total energy delivery during either the stand-by or ready states, respectively 306–308. The user cannot change these same parameters while in the operational state 310. At the end of the total procedure time or the maximum energy end point, the system terminates operation and returns to the ready state 308.

In the operational state, the power control and measurement unit 200 operates within either user-defined parameters input with buttons 122 as well as those control parameter stored in the control/target parameter file 236. The control/ master processor and the power delivery module 216 monitor power and temperature delivered to the surgical instrument and adjust the power accordingly. The unit moves from the operational state to the ready state when the user toggles foot switch 104. The unit moves from the operational state to fatal fault state 314 when a fatal fault error is detected. Alternately, if in the operational state 310 an out of bounds condition is detected for impedance, control passes to impedance fault state process 312.

In process 312 a determination is made as to whether impedance is outside an acceptable range. A high impedance might indicate that the surgical device has been removed from the surgical site. Alternately, if the impedance is too low there may be an equipment malfunction. In this event the control processor 204 returns the unit to either the stand-by state, the device fault state 316, the device self-test state 304, or the fatal fault state 314, depending on the nature of the fault.

Figure 4A:
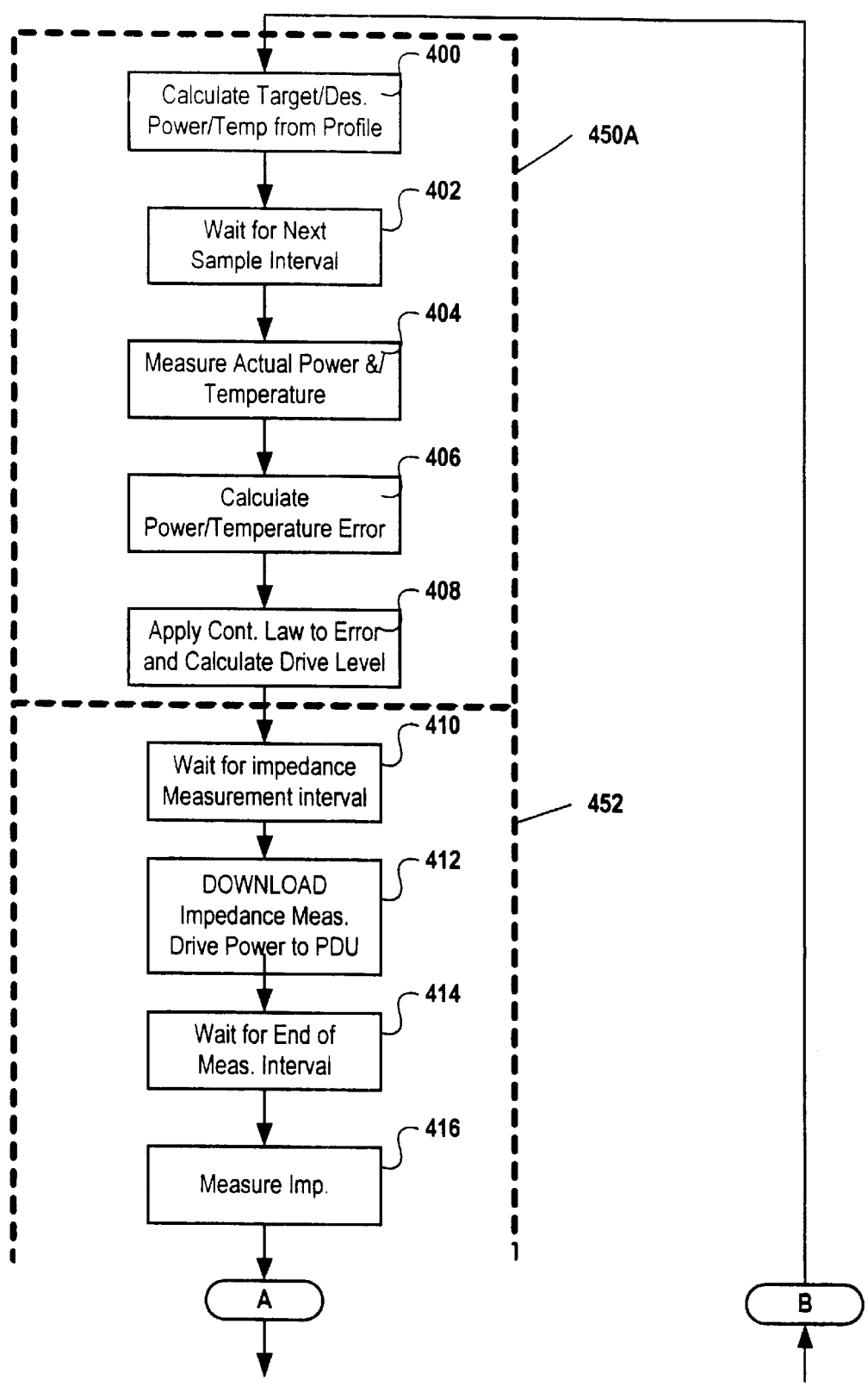
FIGS. 4A–B are process flow diagrams of the power delivery and measurement functions of the master processor.
Figure 4B:
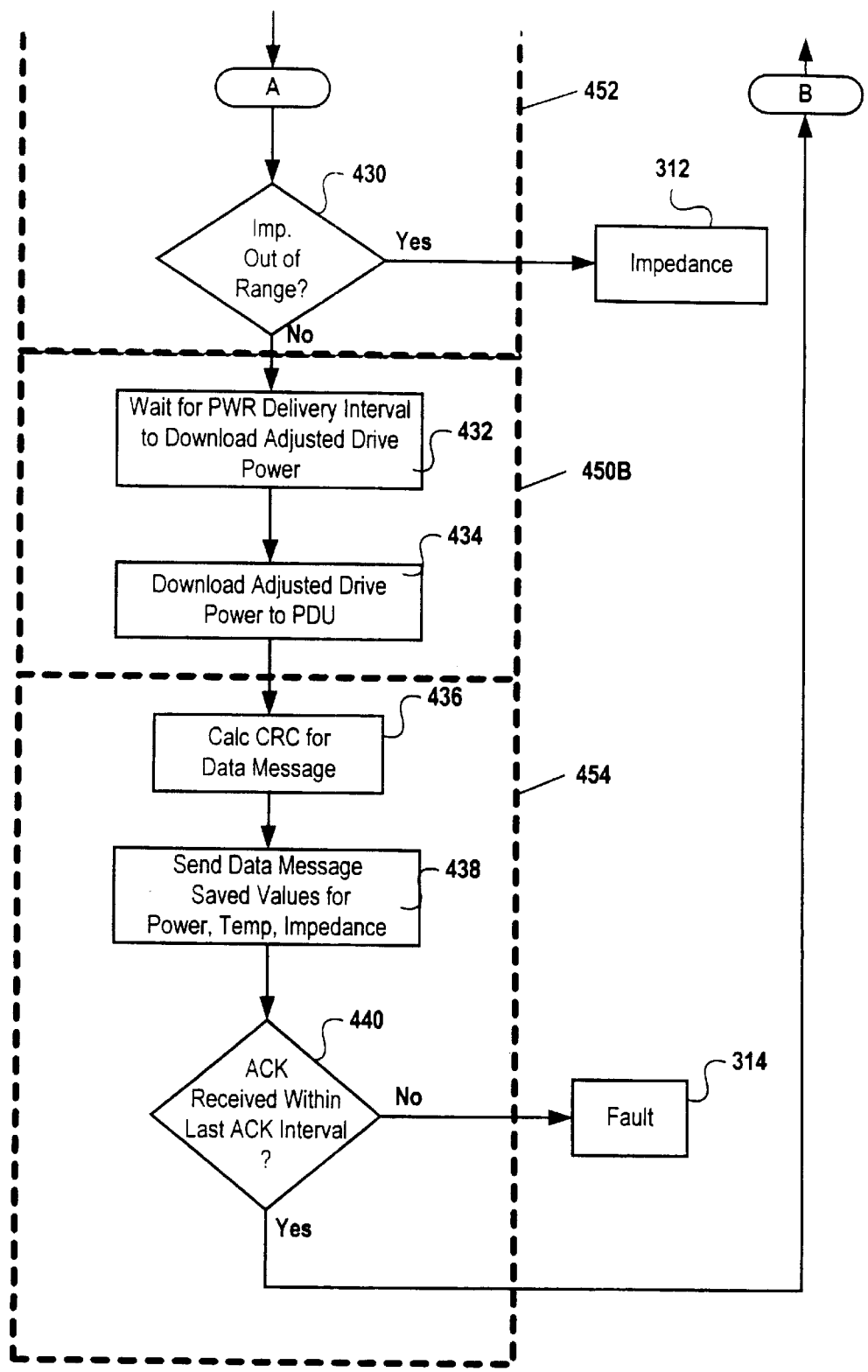

FIGS. 4A–B are process flow diagrams FIGS. 4A–B are process flow diagrams of the power delivery and measurement functions of the master processor 204 (see FIG. 2). There are four primary subroutines dealing with respectively drive level error determination 450A, impedance error determination 452, drive level adjustment 450B and parameter passing 454. Subroutines 450A–B and 452 are implemented for each channel. All subroutines are sequentially engaged in throughout the course of the operational state 310 (see FIG. 3).

Processing in the drive level error determination subroutine 450A begins with process 400. In process 400 a total elapsed time since the commencement of the operational state is updated and a corresponding power or temperature level is obtained by the control/master processor 204 from the control/target parameter file 236 (see FIG. 2). Control is then passed to process 402. In process 402 a wait state is introduced until the start of the next power and/or temperature sampling interval. At the start of that interval control is passed to process 404. In process 404 the power sensing circuit 214 (see FIG.2) measures the actual power delivered to the device during the sample interval. During that same interval the temperature sensing circuit 212 measures the temperature at the surgical site at which the probe of surgical instrument 106, e.g. the probe portion thereof (see FIG. 1) is positioned. Control is then passed to process 406. In process 406 the actual power and/or temperature level is compared with the targeted power and temperature profile discussed above in connection with process 400. The error for each of those parameters between the targeted value and the actual value is calculated. Control is then passed process 408. In process 408 an appropriate control law algorithm is applied to the error to calculate a new drive level which is stored for use in process 432 (see FIG. 4B). Control then passes to subroutine 452 for the measurement of the impedance of the channel being measured.

The impedance measurement is in a preferred embodiment of the invention distinct from the power measurement. They occur at different time interval within an overall cycle that transitions from impedance measurement to heating of the surgical site and then repeats itself. Additionally, if the impedance measurement interval for each channel is a fraction of the heating/power delivery interval for that channel the impact on the surgical site in terms of temperature rise, etc. is limited. No appreciable surgical activity, i.e. cauterizing, cutting, or ablation need take place during the impedance measurement. This has the advantage of allowing impedance measurements to be made at drive levels in excess of those utilized during the actual heating/power delivery interval (see process 432) which provides for a more accurate impedance determination by reducing the effects of background "noise".

In still another embodiment of the invention, not only is the impedance measurement interval short, but it is also time division multiplexed (TDM) between the separate channels. High power levels are only applied for short intervals to a single channel at a time while the other channels are placed in a high impedance state. This avoids crosstalk between multiple electrodes that may be positioned on probe 108 thereby allowing for an accurate impedance measurement.

Processing in subroutine 452 commences with process 410. In process 410 a wait state is introduced pending the start of the impedance measurement interval. Control then passes to process 412 at the start of the impedance measurement interval. In process 412 an elevated drive level appropriate for impedance measurement is downloaded by the CPU to the power delivery module 216 (see FIG. 2). This is 5 watts in this embodiment of the invention. Control is then passed to state/process 414 in which a wait state is introduced to the end of the impedance measurement interval. Control subsequently passes to process 416. In process 416, the impedance of the corresponding channel is calculated. Control then passes through splice block A to the continuation of subroutine 252 shown on FIG. 4B, and specifically decision process 430.

In decision process 430, the control/master processor 204 using target impedance ranges contained in control/target parameter file 236 (see FIG. 2) determines whether or not the measured impedance is out of a range. If the impedance is too low there may be an electrical malfunction. If the impedance is too high the electrode coupled to the channel may be coated with carbonated tissue, or the probe may have been removed from the surgical site. Control is then passed to process 312 (see FIG. 3), where a determination is made as to the cause of the out of range condition. Control is then passed to the appropriate state shown in FIG. 3. If, alternately impedance of the channel being measured is in range, control is passed to subroutine 450B.

Adjustment of the desired drive level of each channel is accomplished in subroutine 450B. Processing begins at process 432. In process 432, a wait state is introduced for the beginning of the power/heating delivery interval. Control is then passed at the start of that interval to process 434. In process 434, the drive level for the next heating interval calculated and stored above in connection with process 408 by the control/master processor 204 is downloaded to the power delivery module 216 (see FIG. 2). That drive level is applied over the heating interval to the corresponding channel. Control then passes to subroutine 454.

Parameter and data sending from the control/master processor 204 to the display processor 206 (see FIG. 2) is handled in subroutine 454. Processing begins at process 436 in which data and parameters to be passed to the display processor, e.g. power, temperature, and impedance for each channel are put in the payload portion of a message. Then a check is performed to assist the display processor in evaluating the integrity of the message it will receive. In an embodiment of the invention a cyclical redundancy calculation (CRC) is performed on the payload and added to the header of the message. Control is then passed to process 438. In process 438, the message packet 240A is passed over by directional serial bus 240 to the display processor 206 of the display unit 202 (see FIG. 2). Control is then passed to decision process 440. In decision process 440 the control processor waits for an acknowledge signal 240B from the display/slave processor 206 indicating that the package has been received and that the CRC calculated by the display processor for the package corresponds with the CRC calculated in process 422 above. If no such acknowledgment is received, control passes to process 314. In process 314 (see FIG. 3) a fatal fault state is entered and the operation of the power control and measurement unit 200 is terminated. If alternately in decision process 426 an acknowledgment is received then control returns to the aforementioned process 400 (see FIG. 4A). The processing of each channel over the next impedance and heating intervals is then re-initiated.

In this embodiment the entire cycle repeats once each second. The temperature sampling interval is coincident with the last 100 milliseconds of the power delivery or heating interval. The power delivery interval 432 lasts for 900 milliseconds out of the one second cycle and the impedance measurement interval 410 is the 100 milliseconds of the 1 second cycle which is completely outside of the 900 milliseconds occupied by power delivery interval. The impedance measurement interval of each channel has a duration of 10 milliseconds for each channel.

Figure 5:
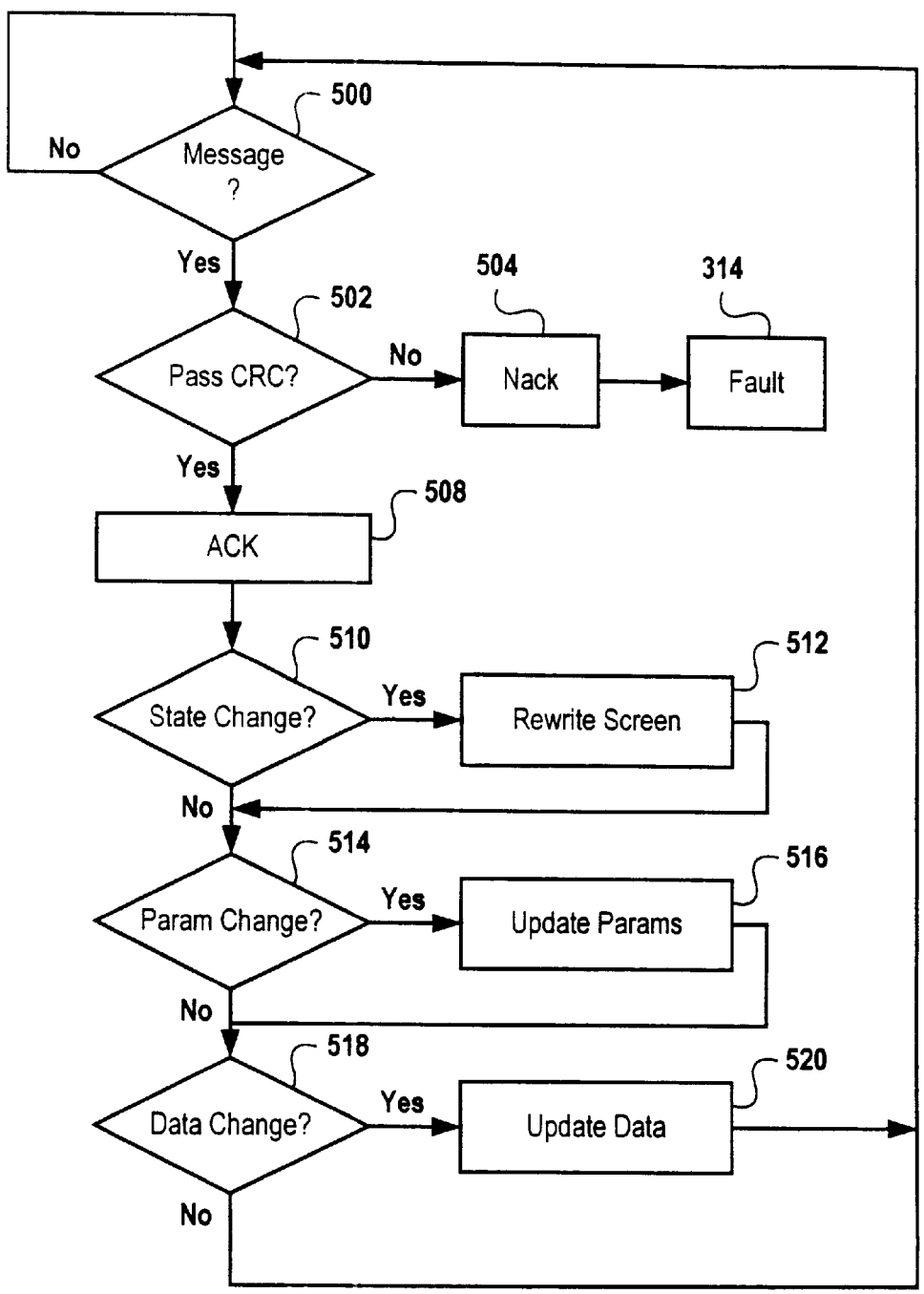
FIG. 5 is a process flow diagram of the GUI display functions performed by the slave processor.

FIG. 5 is a process flow diagram for the processes associated with message passing as implemented on the display processor 206. Processing begins at decision process 500 in which a determination is made that the next message is received. If that determination is in the affirmative control passes to decision process 502. In decision process 502, the CRC for the message is independently calculated by the display processor and compared with the CRC in the header of the message as calculated by the master/control processor 204 (see FIG. 2). If the two do not match, control passes to process 504. In process 504, a NACK response 240B is sent from the display processor to the control processor 204. The display processor control then passes to process 314 in which the display processor enters the fault state (see FIG. 3). If alternately in decision process 502 the calculated CRC of the display processor and the control processor matches then control passes to process 508 and an acknowledge ACK is sent from the display processor 206 to the control processor 204 (see FIG. 2). Control then passes to decision process 510.

In decision process 510, a state field 612 (see FIG. 6A) is read in the message to determine whether the state has changed from, e.g. standby state 306, ready state 308, or operational state 310 (see FIG. 3). If an affirmative decision is reached i.e. that the state has changed then control is passed to process 512. In process 512, the display processor utilizing the receiving parameter 230B and display processes (see FIG. 2) refreshes the display 120 (see FIG. 1) with the appropriate graphical user interface for the new state. Control subsequently passes to decision process 514. Control also passes to decision process 514 from decision process 514 directly if there has been no state change.

In decision process 514 a determination is made as to whether any of the parameters received in the message packet 240A have changed from their previous values. If a determination in the affirmative is reached then control passes to process 516. In process 516, the new parameters are updated for that portion of the graphical user interface in which parameters are listed (see FIGS. 8–9). Control then passes to decision process 518. Control also passes to decision process 518 directly if a negative determination is reached in decision process 514 i.e. that no parameter changes have taken place.

In decision process 518 a determination is made as to whether any of the data, e.g. temperature and impedance, contained in the message has changed from previous values. If the determination is in the affirmative control is passed to process 520. In process 520, the updated parameters are written to the appropriate location of the GUI on the display 120 (see FIGS. 8–10). Control then returns to decision process 500 for the reception of the next message. If alternately in decision process 518 no data change is indicated in the message packet then control returns directly to decision process 500 for the detection of the next message. All the processes discussed above in connection with FIG. 5 are carried out by the display processor 206. The only message that the display processor can send to the control processor is the acknowledge ACK or the not acknowledge NACK.

FIG. 6A shows the header portion 600 of a message and specifically the byte sequence 600A and the corresponding data 600B which the control/master processor 204 can send to the display processor 206 (see FIG. 2). FIG. 6B shows a table 602 with the various parameters 602A–B a message may contain. The parameter message is sent any time any parameter has changed and needs to be updated in the display processor. Reference 610 is the ASCII character that indicates that this message is a parameter message. Reference 612 is the field whose contents indicates what state the control processor was in when the message was sent. Possible states include: power-up reset, system self test, device self test, standby, ready, operational impedance fault, device fault or fatal fault. Reference 616 is the beginning of the cyclical redundancy check field in the message. Reference 614 is the parameter field, the contents of which are set forth in table 602A–B. The value immediately follows the parameter field. The types of parameters are target temperature 630, maximum power, end-point energy, end-point time or model select. By way of example, if the operator pressed the time end-point increment button while in the standby state, the following message would be sent. The field 610 would have the content "P" for parameter message. The state field 612 would have the content indicating a standby state. The field 614 would indicate that the parameter type is time end-point. The value low byte and high byte would have the actual time endpoint, and the cyclical redundancy check would be calculated for the message and put in field 616.

FIG. 7 shows the structure of the payload 700 for a data message that the control processor can send to the display processor. The payload is shown with the byte sequence 700A and a corresponding parameter 700B for a data payload. The data message shown in reference 438 in FIG. 4B is being transmitted by the control processor and is being received by the display processor in reference 500 in FIG. 5. Reference 710 indicates that the message is a data message. Reference 712 indicates what state the control processor was in when the data message was sent and all the following fields in the data message are the current values of the data. For example, reference 714 is the most significant byte of the temperature for channel number 0.

Figure 8:
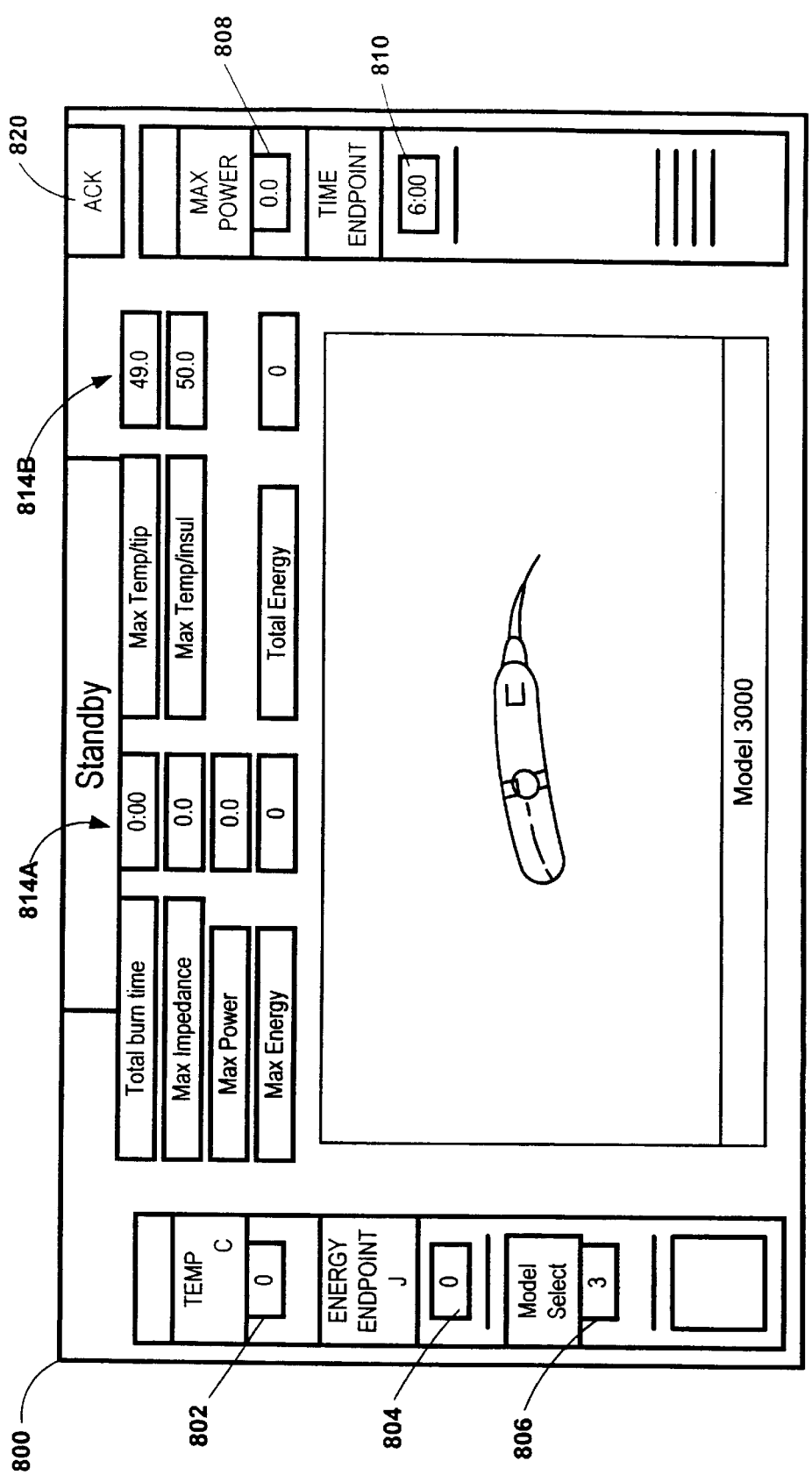
FIG. 8 shows a GUI for Standby mode of the electro-surgical device.

FIG. 8 shows the appearance of the standby GUI 800 generated by the display processor in the standby state 306

(see FIG. 3). Fields 814A–B show the total burn time, maximum impedance, maximum power, maximum energy, maximum tip temperature, maximum insulation temperature and total energy. The temperature is shown in field 802, the energy endpoint in field 804, the model selection for the surgical instrument in field 806, the ACK/NACK status in field 820, the maximum power in field 808 and the time endpoint in field 810. Anytime a message is sent from the control processor to the display processor while the control processor is in the standby state the display processor will go into the standby state and display the screen in FIG. 8.

Figure 9:
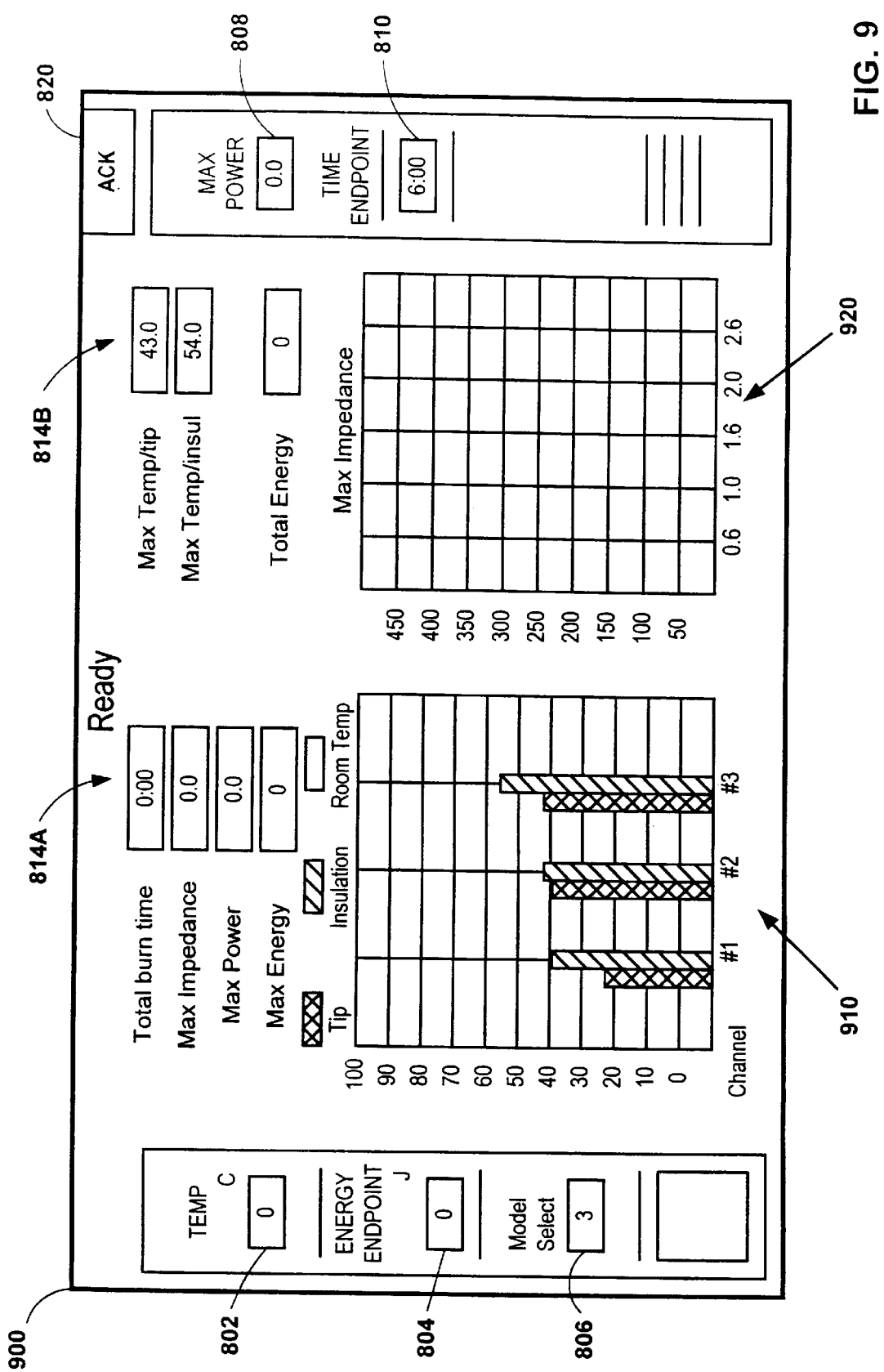
FIG. 9 shows a GUI for Ready mode of the electro-surgical device.

FIG. 9 shows the GUI 900 of the display processor in the ready state. As in the case of the standby screen in FIG. 8, these screens are shown when the display processor enters the corresponding state. For example, if the control processor was in the ready state when a message was sent it would put the display processor into the ready state by the state field 612 in the header of the message (see FIG. 6). In response the display processor would select the appropriate GUI and fill in the corresponding data and parameters. In the ready state fields 814A–B show the total burn time, maximum impedance, maximum power, maximum energy, maximum tip temperature, maximum insulation temperature and total energy. The temperature is shown in field 802, the energy endpoint in field 804, the model selection for the surgical instrument in field 806, the ACK/NACK status in field 820, the maximum power in field 808 and the time endpoint in field 810. In addition temperature samples 910 for each channel are displayed along with impedance samples 920. The data for these samples is contained in the payload of a ready message. Reference 920 shows the maximum impedance, meaning the highest impedance of any active channel, this information also having been obtained from the data message of FIG. 7.

Figure 10:
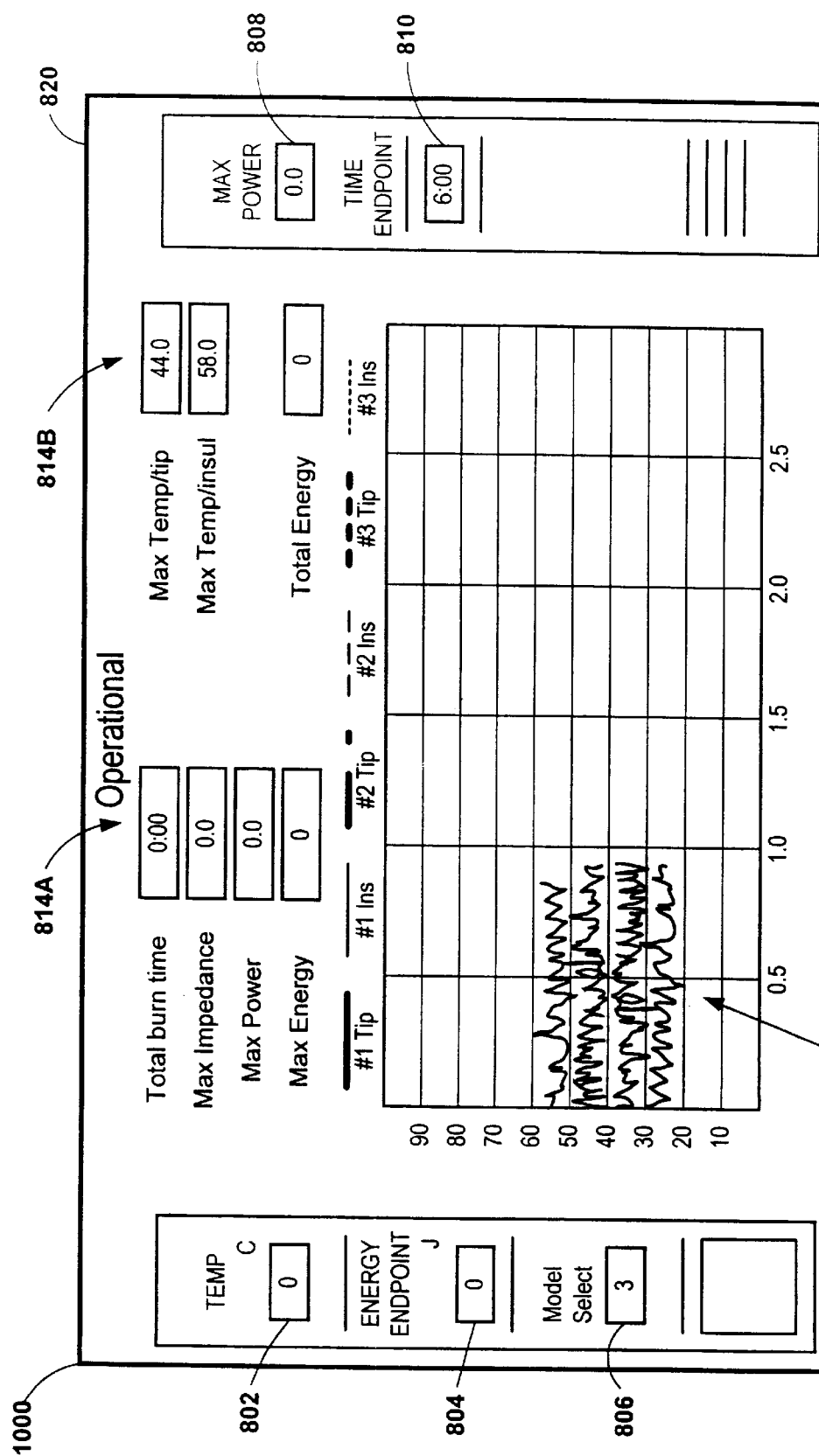
FIG. 10 shows a GUI for Operational mode of the electro-surgical device.

FIG. 10 shows the GUI 1000 of the display processor in the operational state. In the operational state fields 814A-B show the total burn time, maximum impedance, maximum power, maximum energy, maximum tip temperature, maximum insulation temperature and total energy. The temperature is shown in field 802, the energy endpoint in field 804, the model selection for the surgical instrument in field 806, the ACK/NACK status in field 820, the maximum power in field 808 and the time endpoint in field 810. In addition a graph 1002 of the temperature of each device tip as a function of time is displayed. These temperatures are also obtained from the data messages shown in FIG. 7.

Although the foregoing invention has been described in detail for purposes of clarity of understanding, it will be obvious that certain modifications may be practiced within the scope of the appended claims.

What is claimed is:

1. A method for providing a graphical user interface in an electro-surgical instrument with a power delivery channel, at least one electrode and a display, and the electro-surgical instrument for delivering power to a surgical site, and the method for providing comprising the acts of:

controlling with a control unit the operation of the power delivery channel and at least one electrode to deliver power to the surgical site;

determining with the control unit at least one parameter of the power delivery channel and computing for the at least one parameter a first error detection indicia;

passing the at least one parameter and the first error detection indicia from the control unit to a display unit;

accepting at the display unit the at least one parameter and verifying the integrity of the at least one parameter utilizing the first error detection indicia and a second error detection indicia calculated by the display unit; and displaying the at least one parameter on a graphical user interface generated by the display unit.

2. The method of claim 1, wherein the verifying act further comprises the act of:

notifying the control unit of a loss of integrity of the least one parameter.

3. The method of claim 2, further comprising the act subsequent to the accepting act of:

terminating operation of the power delivery channel responsive to said notifying act.

4. The method of claim 1, wherein the first error detection indicia in said act of computing comprises a cyclical redundancy check.

5. The method of claim 1, wherein the accepting and displaying acts are implemented utilizing non-verified program code.

\* \* \* \* \*